(12) United States Patent
Garfield et al.

(10) Patent No.: US 7,820,100 B2
(45) Date of Patent: Oct. 26, 2010

(54) SYSTEM AND METHOD FOR PHOTOCATALYTIC OXIDATION AIR FILTRATION USING A SUBSTRATE WITH PHOTOCATALYST PARTICLES POWDER COATED THEREON

(75) Inventors: Kirk Garfield, Irving, TX (US); John Potter, Plano, TX (US)

(73) Assignee: Garfield Industries, Inc., Addison, TX (US)

( * ) Notice: Subject to any disclaimer, the term of this patent is extended or adjusted under 35 U.S.C. 154(b) by 616 days.

(21) Appl. No.: 11/750,201

(22) Filed: May 17, 2007

(65) Prior Publication Data

US 2008/0286163 A1 Nov. 20, 2008

(51) Int. Cl.
*A61L 9/00* (2006.01)
*A61L 2/00* (2006.01)
*B01J 19/08* (2006.01)
*G01N 23/00* (2006.01)
*H01B 1/02* (2006.01)
*C01B 21/26* (2006.01)
*C01C 1/245* (2006.01)
*B01D 39/00* (2006.01)

(52) U.S. Cl. ............ 422/1; 422/5; 422/24; 422/186.04; 422/186.3; 422/292; 250/455.11; 252/514; 423/403; 423/546; 96/224

(58) Field of Classification Search ............ 422/1, 422/5, 24, 186.04, 186.3, 292; 250/455.11; 252/514; 423/403, 546; 96/224

See application file for complete search history.

(56) References Cited

U.S. PATENT DOCUMENTS

| | | | |
|---|---|---|---|
| 4,004,324 A | 1/1977 | Bridge et al. | 19/156.3 |
| 4,282,206 A | 8/1981 | Warner, Jr. et al. | 424/59 |
| 4,814,412 A | 3/1989 | Crowther et al. | 528/28 |
| 4,892,712 A | 1/1990 | Robertson et al. | 422/186 |
| 4,966,759 A | 10/1990 | Robertson et al. | 422/186 |
| 5,421,048 A | 6/1995 | Reinert, Sr. | 8/158 |
| 5,490,983 A | 2/1996 | Worley et al. | 424/405 |
| 5,511,263 A | 4/1996 | Reinert, Sr. | 8/158 |
| 5,513,407 A | 5/1996 | Reinert, Sr. | 8/158 |
| 5,564,065 A | 10/1996 | Fleck et al. | 422/186.3 |
| 5,582,632 A | 12/1996 | Nohr et al. | 95/78 |
| 5,591,690 A | 1/1997 | King et al. | 502/401 |
| 5,616,532 A | 4/1997 | Heller et al. | 502/242 |
| 5,622,543 A | 4/1997 | Yang | 96/58 |

(Continued)

FOREIGN PATENT DOCUMENTS

WO 2004/024834 3/2004

OTHER PUBLICATIONS

APH Product Information for AirSoPure S-900 Purifier; http://www.air-purifier-home.com /product/S900.aspx, pp. 1-4 (access date Oct. 23, 2006).

(Continued)

*Primary Examiner*—Jill Warden
*Assistant Examiner*—Monzer R Chorbaji
(74) *Attorney, Agent, or Firm*—Ayhan E. Mertogul; David G. Rosenbaum; Rosenbaum & Silvert, P.C.

(57) ABSTRACT

The present invention relates to an air filtration system and a method for making a photocatalytic oxidation substrate by powder coating a photocatalyst onto a metal substrate.

10 Claims, 8 Drawing Sheets

U.S. PATENT DOCUMENTS

| | | | | |
|---|---|---|---|---|
| 5,652,966 | A | 8/1997 | Reinert, Sr. | 2/457 |
| 5,670,646 | A | 9/1997 | Worley et al. | 548/301.1 |
| 5,681,533 | A | 10/1997 | Hiromi | 422/121 |
| 5,709,735 | A | 1/1998 | Midkiff et al. | 96/17 |
| 5,790,934 | A | 8/1998 | Say et al. | 422/186 |
| 5,808,089 | A | 9/1998 | Worley et al. | 548/318.5 |
| 5,835,840 | A | 11/1998 | Goswami | 422/186.3 |
| 5,849,200 | A * | 12/1998 | Heller et al. | 210/748 |
| 5,854,169 | A | 12/1998 | Heller et al. | 502/242 |
| 5,889,130 | A | 3/1999 | Worley et al. | 526/261 |
| 5,919,422 | A | 7/1999 | Yamanaka et al. | 422/121 |
| 5,933,702 | A * | 8/1999 | Goswami | 422/186.3 |
| 5,954,869 | A | 9/1999 | Elfrersy et al. | 106/287.16 |
| 5,959,014 | A | 9/1999 | Liebeskind et al. | 524/389 |
| 6,020,491 | A | 2/2000 | Wonley et al. | 544/220 |
| 6,063,343 | A | 5/2000 | Say et al. | 422/186.3 |
| 6,093,676 | A | 7/2000 | Heller et al. | 502/242 |
| 6,099,798 | A | 8/2000 | Kambe et al. | 422/24 |
| 6,113,815 | A | 9/2000 | Elfersy et al. | 252/588 |
| 6,117,337 | A | 9/2000 | Gonzalez-Martin | 210/748 |
| 6,120,587 | A | 9/2000 | Elfersy et al. | 106/18.35 |
| 6,121,191 | A * | 9/2000 | Komatsu et al. | 502/330 |
| 6,122,877 | A | 9/2000 | Hendrickson et al. | 52/520 |
| 6,136,186 | A | 10/2000 | Gonzalez-Martin | 210/198.1 |
| 6,159,421 | A * | 12/2000 | Fujii | 422/4 |
| 6,162,535 | A | 12/2000 | Turkevich et al. | 428/372 |
| 6,221,944 | B1 | 4/2001 | Liebeskind et al. | 524/386 |
| 6,241,856 | B1 | 6/2001 | Newman et al. | 204/157.3 |
| 6,254,712 | B1 | 7/2001 | Enlow et al. | 156/244.11 |
| 6,294,185 | B1 | 9/2001 | Worley et al. | 424/405 |
| 6,350,399 | B1 | 2/2002 | Cook et al. | 264/129 |
| 6,376,565 | B1 | 4/2002 | Dyer et al. | 521/64 |
| 6,423,363 | B1 | 7/2002 | Traska et al. | 426/604 |
| 6,440,266 | B1 | 8/2002 | George et al. | 162/101 |
| 6,447,731 | B1 | 9/2002 | Sun et al. | 422/121 |
| 6,462,947 | B1 | 10/2002 | Huang | 361/695 |
| 6,469,120 | B1 | 10/2002 | Elfersy et al. | 528/29 |
| 6,491,883 | B2 | 12/2002 | Mori et al. | 422/306 |
| 6,506,873 | B1 | 1/2003 | Ryan et al. | 528/354 |
| 6,508,992 | B1 | 1/2003 | Taoda et al. | 422/186.3 |
| 6,515,422 | B1 | 2/2003 | Honda | 313/635 |
| 6,524,457 | B1 | 2/2003 | Scott | 204/490 |
| 6,524,536 | B2 | 2/2003 | Newman et al. | 422/122 |
| 6,531,100 | B1 | 3/2003 | Ogata et al. | 422/177 |
| 6,547,912 | B2 | 4/2003 | Enlow et al. | 156/244.23 |
| 6,558,639 | B1 | 5/2003 | Watanabe et al. | 422/186.3 |
| 6,613,277 | B1 | 9/2003 | Monagan | 422/24 |
| 6,620,385 | B2 | 9/2003 | Fujii | 422/186.3 |
| 6,632,805 | B1 | 10/2003 | Liebeskind et al. | 514/63 |
| 6,649,561 | B2 | 11/2003 | Sangiovanni et al. | 502/300 |
| 6,682,814 | B2 | 1/2004 | Hendrickson et al. | 428/326 |
| 6,685,891 | B2 | 2/2004 | Benda et al. | 422/186.3 |
| 6,716,406 | B2 | 4/2004 | Reisfeld et al. | 423/245.1 |
| 6,737,020 | B1 | 5/2004 | Horton, III et al. | 422/24 |
| 6,752,957 | B1 | 6/2004 | De Lasa et al. | 422/22 |
| 6,761,859 | B1 | 7/2004 | Oda | 422/186.3 |
| 6,762,172 | B1 | 7/2004 | Elfersy et al. | 514/63 |
| 6,764,655 | B1 | 7/2004 | Nishii et al. | 422/122 |
| 6,773,682 | B1 | 8/2004 | Benda | 422/186.3 |
| 6,773,804 | B2 | 8/2004 | Enlow et al. | 428/327 |
| 6,783,740 | B2 | 8/2004 | Colby et al. | |
| 6,797,127 | B1 | 9/2004 | Murata et al. | 204/158.2 |
| 6,833,122 | B2 | 12/2004 | Reisfeld | 422/186.3 |
| 6,835,359 | B2 | 12/2004 | Taoda et al. | 422/186.3 |
| 6,838,059 | B2 | 1/2005 | Taoda et al. | 422/186.3 |
| 6,858,551 | B1 | 2/2005 | Turkevich et al. | 442/414 |
| 6,866,828 | B2 | 3/2005 | Segawa et al. | 422/186.04 |
| 6,884,399 | B2 | 4/2005 | Reisfeld et al. | 422/186.3 |
| 6,902,653 | B2 | 6/2005 | Carmignani et al. | 204/157.15 |
| 6,911,174 | B2 | 6/2005 | Creagan | 264/444 |
| 6,933,252 | B2 | 8/2005 | Pierce | 442/327 |
| 6,939,397 | B2 | 9/2005 | Nelsen et al. | 96/224 |
| 6,989,125 | B2 | 1/2006 | Boney et al. | 264/465 |
| 7,001,562 | B2 | 2/2006 | Schiffer et al. | 264/491 |
| 7,028,478 | B2 | 4/2006 | Prentice, III | 60/645 |
| 2002/0029955 | A1 | 3/2002 | Sahle-Demessie | 204/157.15 |
| 2002/0033327 | A1 | 3/2002 | Benda et al. | 204/158.2 |
| 2002/0035162 | A1 | 3/2002 | Newman et al. | 516/98 |
| 2002/0094298 | A1 | 7/2002 | Monagan | 422/5 |
| 2002/0170815 | A1 | 11/2002 | Fujii | 204/157.3 |
| 2003/0019738 | A1 | 1/2003 | Reisfeld et al. | 204/157.3 |
| 2003/0086831 | A1 | 5/2003 | Horton, III | 422/120 |
| 2003/0150707 | A1 | 8/2003 | Carmignani et al. | 204/157.3 |
| 2003/0150708 | A1 | 8/2003 | Fink | 204/157.3 |
| 2003/0180200 | A1 | 9/2003 | Reisfeld | 422/186.3 |
| 2003/0183503 | A1 | 10/2003 | Fujii | 204/157.3 |
| 2003/0211022 | A1 | 11/2003 | Gross et al. | 422/292 |
| 2003/0230477 | A1 | 12/2003 | Fink et al. | 204/157.3 |
| 2004/0007453 | A1 | 1/2004 | Scahill et al. | 204/157.3 |
| 2004/0040832 | A1 | 3/2004 | Kartheuser et al. | 204/157.3 |
| 2004/0071589 | A1 | 4/2004 | Morneault et al. | 423/4 |
| 2004/0130271 | A1 * | 7/2004 | Sekoguchi et al. | 315/111.81 |
| 2004/0166037 | A1 | 8/2004 | Youdell et al. | 422/186.3 |
| 2004/0175304 | A1 | 9/2004 | Reisfeld et al. | 422/186.3 |
| 2005/0063881 | A1 | 3/2005 | Senne et al. | 422/186.3 |
| 2005/0118078 | A1 | 6/2005 | Dobbs et al. | 422/186.3 |
| 2005/0191219 | A1 | 9/2005 | Uslenghi et al. | 422/186.3 |
| 2005/0224335 | A1 | 10/2005 | Carmignani et al. | 204/157.15 |
| 2005/0244309 | A1 | 11/2005 | Wang | 422/186.3 |
| 2006/0032199 | A1 | 2/2006 | Beam et al. | 55/471 |
| 2006/0057020 | A1 | 3/2006 | Tufo | 422/24 |
| 2006/0116279 | A1 * | 6/2006 | Kogoi et al. | 502/103 |
| 2006/0120929 | A1 | 6/2006 | Ward et al. | 422/186.3 |
| 2006/0124442 | A1 | 6/2006 | Valpey, III, et al. | 204/157.15 |
| 2006/0135688 | A1 | 6/2006 | Gibson et al. | 524/783 |
| 2006/0144690 | A1 | 7/2006 | Fink et al. | 204/157.5 |
| 2006/0153749 | A1 | 7/2006 | Schroder | 422/186.3 |
| 2006/0182670 | A1 | 8/2006 | Allen | 422/186.3 |
| 2006/0278075 | A1 * | 12/2006 | Blackner | 95/57 |
| 2006/0280660 | A1 | 12/2006 | Weiss | 422/186.3 |

OTHER PUBLICATIONS

Ginestet, A., et al., "Development of a new photocatalytic oxidation air filter for aircraft cabin", *Indoor Air*, 15(5):326-334; Oct. 2005 (Abstract).

Jianghu Product Information, http://jianhu.en.alibaba.com/product/50032801/50149676/Titanium_Dioxide_Rutile/Tit... pp. 1-3 (access date Oct. 26, 2006).

Peak Pure Air, Air Oasis™ Air Purifier UV Air Cleaner Product Information, http://www.peakpureair.com/airoasis.htm, pp. 1-8 (access date Oct. 24, 2006).

Pennisi, Mario S., "Powder Coating", http://www.finishing.com/Library/pennisi/powder.html, pp. 1-5 (access date Oct. 25, 2006).

Stevens, L., et al., "Photocatalytic Oxidation of Organic Pollutants Associated with Indoor Air Quality", for Presentation at the Air & Waste Management Association's $91^{st}$ Annual Meeting and Exhibit, pp. 1-8, (Jun. 14-18, 1998).

"Degussa Technical Information for AEROXIDE and AEROPERL Titanium Dioxide as Photocatalyst", pp. 1-14 (Dec. 2005).

"Electrostatic Spray", SpecialChem Innovation & Solutions, http://www.specialchem4coatings.com/tc/powder-coatings/index.aspx?id=electrostatic, p. 1, (Oct. 8, 2007).

"Powder Coating Process", SpecialChem Innovation & Solutions, http://www.specialchem4coatings.com/tc/powder-coatings/index.aspx?id=process, p. 1, (Oct. 8, 2007).

"Major Resin Types", SpecialChem Innovation & Solutions, http://www.specialchem4coatings.com/tc/powder-coatings/index.aspx?id=resin, p. 1-2, (Oct. 8, 2007).

"Thermoplastic Coating", Plastics Dome, http://plastics.turkavkaz.ru/processes/coating/ p. 1-2, (Oct. 8, 2007).

"How is Electrostatic Spraying Done?", Brothers Power Coating, p. 1, http://www.brotherspowdercoating.com/what-is-powder-coating.html, (Oct. 8, 2007).

"The Complete Solution to Indoor Air Polutionlems", Second Wind Air Purifier Systems, p. 1-8, http://www.texansmechanical.com/iaq.html, (Oct. 24, 2006).

"Powder Coating Systems", Fischer Finishing Systems, p. 1, http://www.fischerindustrial.com/powder_systems.html, (Oct. 8, 2007).

"Welcome to Garfield Industries, Inc.", Garfield Industries, Inc., p. 1, http://garfieldindustries.com/, (Oct. 8, 2007).

"Specification: Model GTR-12-020-A or E", Garfield Industries, Inc., GFIFILT02, p. 1-5, (Mar. 21, 2006).

"Specification: Model GTR-12-020-A or E", Garfield Industries, Inc., GFIFILT04, p. 1-6, (Mar. 6, 2003).

"Powder Coating", Wikipedia, p. 1-3, http://en.wikipedia.org/wiki/Powder_coating, (Oct. 8, 2007).

"Versatial—Economical and Envrironmentally Friendly", ProCoat Power Coating, Home Page, p. 1-2, http://www.procoatpowdercoating.com/, (Oct. 8, 2007).

Daniel M. Blake, "Bibliography of Work on the Heterogenous Photocatalytic Removal of Hazardous Compounds from Water and Air Update No. 2 to Oct. 1996", National Renewable Energy Laboratory, NREL/TP-430-22197 UC Category 1600 DE97000084, p. 1-88, (Jan. 1997).

"Product Bulletin: 5 ACLNR—Section 5 Jan. 1, 2006 for Z-Line Series Air Cleaner Filters", Glasfloss Industries, p. 1-4.

"Technical Information for Aeroxide and Aeroperl Titanium Dioxide as Photcatalyst", Bulletin No. 1-1243-0/Dec. 2005, Degussa, Inc., p. 1-14.

Ana M. Peiro, et al, "Electrochemically Assisted Deposition of Titanium Dioxide on Aluminum Cathodes", J of Mat Chem, vol. 12, p. 2769-2773 (2002).

"User's Guide for Portable Unit M-600", Aurora International, Ltd., p. 1-6.

US 6,955,791, 10/2005, Fink et al. (withdrawn)

* cited by examiner

SYSTEM AND METHOD FOR PHOTOCATALYTIC OXIDATION AIR FILTRATION USING A SUBSTRATE WITH PHOTOCATALYST PARTICLES POWDER COATED THEREON

TECHNICAL FIELD OF THE INVENTION

The present invention relates to an air filtration system and a method for photocatalytic oxidation air treatment employing a substrate having a photocatalyst coated thereupon.

BACKGROUND OF THE INVENTION

Ambient environmental air in a home, office, educational, institutional, industrial or institutional setting can be a contributing factor in maintaining a healthy environment. Particulates, such as pollen, dust, mold, spores, bacteria, viruses, animal dander, skin cells, or the like, and volatile chemicals, including volatile organic compounds, commonly referred to as VOCs, formaldehyde, cleansers, pesticides, fungicides, combustion by-products, odors and toxic gases are frequently present in the ambient air. These airborne elements have been implicated in a wide variety of respiratory conditions and diseases.

Often times, the indoor level of air pollution can be exponentially higher than outdoor levels because of the sealed nature of the indoor environment. Given that the majority of people spend most of their time indoors at school, work or at home, control over the ambient air quality may be a significant factor in maintaining good health.

A wide variety of air treatment devices and methods are known in the art. One approach employs HEPA (High Efficiency Particulate Air) filters which can collect almost 100% of airborne particles greater than 0.3 microns in diameter. Another approach involves electrostatic precipitators which use electrostatic forces to remove particles from the air and is able to collect particles down to a diameter of 0.01 microns. However, neither HEPA filters nor electrostatic precipitators have demonstrated ability to remove volatile organics compounds (VOCs) from the air, and thus can do nothing to reduce odors or the health effects of the VOCs in the air.

One approach for treating air involves photocatalytic oxidation (PCO) technology. PCO technology has been used to remove organic contaminants and compounds from air fluid streams. In commonly used institutional air filtration systems that incorporate PCO technology, the PCO system used generally include one or more ultraviolet (UV) energy sources for irradiating UV light onto a substrate with a titanium dioxide coating. Disintegration of organic compounds takes place through reactions with oxygen ($O_2$) and hydroxyl radicals (OH). The $O_2$ and OH reactions with VOCs drive these diverse gas-phase odor causing contaminants to change their chemical make-up, thereby reducing odors.

While complete oxidation without a photocatalyst is thermodynamically possible, this process is kinetically slow and is not, therefore, institutionally feasible. Although various photocatalysts have been used in PCO air filtration systems, titanium dioxide ($TiO_2$) remains the most popular and most prevalent because of advantageous characteristics. Titanium dioxide is generally accepted as a light, strong, and anti-corrosive compound that, if scratched or damaged, will immediately restore the oxide in the presence of air or water.

Currently, there is still not a complete picture of the exact mechanism by which titanium dioxide, oxygen ($O_2$) and UV light oxidize organic compounds. Nonetheless, experimental evidence from reaction rates at varying concentrations suggests that the oxidation reaction takes place on the photocatalyst surface. When excited by radiation, titanium dioxide photocatalysts generate electron/hole pairs which act as strong oxidizing agents to adsorbed species. In particular, light with a wavelength less than 400 nm (radiation in the near-UV range) forms these electron/hole pairs in titanium dioxide which are capable of initiating the oxidation reaction with adsorbed molecules. There is evidence from several studies that the reaction proceeds through several intermediates (depending on the complexity of the molecule being oxidized), rather than instantaneously being oxidized to carbon dioxide ($CO_2$). It is this procession through intermediates that makes identification of the specific reaction difficult.

A titanium dioxide film layer is known to have a high refraction ratio. When a titanium dioxide film layer is irradiated by UV light of less than 400 nm, the band gap energy (the level of energy photons needed to be able to free electrons from their atomic bonds) is exceeded. When this occurs, electron/hole pairs and hydroxyl radicals (OH) are created, which causes airborne contaminants, i.e. volatile organic compounds (VOCs), particulates, and bioaerosols, to be attracted to the titanium dioxide. These contaminants are eventually oxidized through a procession of reactions and intermediates concluding with $CO_2$ as the primary end product.

Although the use of titanium dioxide as a photocatalyst for PCO air filtration systems has been widespread, other photocatalysts have also used been used. These photocatalysts include stannic oxide, zinc oxide, vanadium oxide, dibismuth trioxide, tungsten trioxide, ferric oxide, strontium titanate, cadmium suphide, zirconium oxide, antimony oxide, and cerium oxide. The use of these photocatalysts for powder coating onto the surface of a substrate is within the scope of the invention Because of the major role played by the photocatalyst in an oxidation reaction, many improvements to the efficiency of the air filtration process can be made through the photocatalyst itself. One determinant of PCO efficiency involves the form of the photocatalyst used. The photocatalyst titanium dioxide (sometimes also referred to as titania and titanium oxide) can exist in four forms: rutile, anatase, brookite, and as titanium dioxide (B). In the rutile form, titanium dioxide exists as a tetragonal mineral usually of prismatic habit. In the anatase form titanium dioxide exists as a tetragonal mineral of dipyramidal habit. In the brookite form, titanium dioxide exists as an orthorhombic mineral. Lastly, titanium dioxide can also exist in the form commonly referred to as titanium dioxide (B), which is formed of monoclonic materials.

Studies have been done using the high-surface area Degussa P25 form of titanium dioxide (surface area of 50 $m^2/g$) to be highly effective in oxidizing airborne contaminants. Since the oxidation reaction rate is proportional to the photocatalyst surface area, increasing the effective surface of the titanium dioxide film layer can be advantageous.

Another way of improving the efficiency of the oxidation reaction involves improving the activity of the photocatalyst itself. Studies have been conducted on the effects of loading the photocatalyst surface with different metals. In one study, silver nitrate and sodium carbonate were added to a titanium dioxide slurry and dried baked, adding to the titanium dioxide surface. This addition process can greatly increase the efficiency of the PCO process. (Kondo and Jardim, 1991).

Other studies have made similar findings. In one study, it was found that adding platinum, palladium, or gold to the titanium dioxide surface increases oxidation rates by a factor of 3 to 5 and similar results have been obtained by doping the titanium dioxide with tungsten oxide. (Wilkins and Balke, 1994).

The lifetime of the photocatalyst is another important consideration with respect to the economic feasibility of the PCO process. Even though titanium dioxide is a fairly inexpensive compound, frequent replacement would be inconvenient and would decrease the economic viability of a PCO air filtration system. In general, photocatalyst activity should remain relatively constant with moderate use of a PCO air filtration system. However, a major barrier to a long lifetime of the photocatalyst is the adsorption of non-organics, taking up reaction sites on the photocatalyst surface.

Another major barrier to the lifetime of the photocatalyst involves susceptibility of the photocatalyst to chipping and flaking. Often a layer of titanium dioxide coated onto a substrate using a conventional liquid coating process will chip and flake off with repeated use of the PCO air filtration system. Replacing the titanium dioxide coated substrate can be burdensome.

Another relevant component to the PCO air filtration process involves the illumination source. It has been found, in particular, that 253.7 nm ultraviolet (UV) light applied from 36 watt UV lamps exhibits particularly good photocatalytic oxidative activity when used with the present invention. Similar positive results have also been found with 60 watt and 8 watt UV lamps that emit UV light at approximately 253.7 nm. Depending on the particular air filtration applications involved, other UV lamps emitting light at other UV wavelengths and at other power levels are also within the scope of the invention.

Exemplary known PCO air purification systems are represented by U.S. Pat. Nos. 6,884,399, 6,833,122, and 6,716,406 (hereinafter collectively referred to as "Reisfeld"), which describe a PCO air purifier using an aluminum filter substrate coated with titanium dioxide particles. Reisfeld also describes a control system that includes a motion detector and a sensor for detecting contaminant concentration. Nevertheless, Reisfeld does not disclose an air filtration system, wherein titanium dioxide particles are powder coated onto a substrate.

U.S. Pat. Nos. 6,838,059, 6,835,359, and 6,508,992 (hereinafter collectively referred to as "Taoda") also describe a PCO air filtration system. More specifically, Taoda describes coating titanium dioxide (in its anatase form) to increase the specific surface area of the photocatalyst pellets. Furthermore, Taoda also describes coating titania sol by suspending fine titanium dioxide particles in water.

U.S. Pat. No. 6,797,127 to Murata et al. (hereinafter referred to as "Murata") discloses a PCO system, wherein titanium dioxide "is directly adhered to a substrate by a low temperature flame spray coating process without using a binder, and a sol-gel process, that is, a process wherein a sol comprising a photocatalyst (photo-semiconductor particles, and an adsorbing material), a film forming component as inorganic binder, and a solvent is adhered on a substrate and then the sol is gelatinized, for example, at 300 to 400° C." Murata's flame spray coating process involves spraying titanium dioxide onto the substrate "by a gas flame spray coating process using oxygen, acetylene, or the like, together with a ceramic melted at about 2900 to 3000° C."

U.S. 2006/0182670 to Allen (hereinafter referred to as "Allen") also discloses a PCO system. Allen describes the difficulties of depositing titanium dioxide on a surface because this process creates an unstable material. More specifically, Allen notes that the titanium formed from this type of process is prone to flaking off from the surface, and thus would not be able to withstand washing. Allen proposes fixing titanium dioxide on the substrate through impregnation. One of Allen's suggested methods involves impregnating the titanium dioxide while melt-spinning fibers to produce a doped fiber. Another suggested method by Allen involves coating a fiber with titanium dioxide and running it through a heated region to anneal the titanium dioxide to the fiber.

While there currently exist PCO air filtration systems, the current existing systems suffer deficiencies. Heretofore, the preferred process for coating a substrate with titanium dioxide involved conventional liquid coatings, such as a sol-gel process. However, these known processes for coating a substrate with titanium dioxide using conventional liquid coatings suffer drawbacks. For one, a conventional liquid coating will often have longitudinally running and sagging streaks on the substrate. These longitudinal streaks generally become more pronounced with increased coating thickness. The occurrence of longitudinal streaks can cause quality problems in the form of striation, i.e., longitudinal non-uniform coating thickness caused by uneven application of the liquid coating and by longitudinal streaks. It is known in the art that with conventional liquid coatings, horizontally coated surfaces and vertically coated surfaces can have different surface characteristics, e.g., different coating thickness. Thus, the process of coating a substrate with titanium dioxide using conventional liquid coating presents challenging operational constraints, particularly when thicker coatings are desired.

Furthermore, titanium layers formed on a substrate through a conventional liquid coating process have been found to have high incidence of chipping and flaking.

Accordingly, there is a need for a system and method for PCO air filtration using a substrate, wherein titanium dioxide is coated onto the substrate, without the above-mentioned operational constraints, thereby creating a layer of titanium dioxide with substantially uniform thickness. There is also a need for a PCO air filtration system that will effectively destroy bioaerosols (including microorganisms such as bacteria, viruses, mold and dust mites), volatile organic compounds (VOCs including chemical gases, solvents, and odor causing contaminants), and yet is durable and will have a long lifetime.

The discussion of art in this section is not intended to constitute an admission that any patent, publication, or other information referred to is "prior art" with respect to the invention, unless specifically designated as such.

SUMMARY OF INVENTION

In accordance with the invention, there is provided a method for powder coating titanium dioxide onto a substrate for use in a PCO air filtration system. The method for powder coating a photocatalyst onto a substrate used in a photocatalytic oxidation air filtration system comprises the steps of: mixing the photocatalyst with resin to form a photocatalyst mixture; electrostatically charging the photocatalyst mixture; and spraying the photocatalyst mixture onto the substrate.

Air filtration systems incorporating a substrate with titanium dioxide powder coated thereon is also described. A first general embodiment comprises a photocatalytic air purification unit which is adapted to be placed in line in return ductwork of a building HVAC (Heating, Ventilating, and Air Conditioning) system and/or air moving device. In accordance with this first general embodiment, each specific embodiment share the common features comprising: a particulate filter; a substantially rigid honeycomb-like metal substrate which is powder coated with a photocatalyst; at least one UV light source for irradiating UV light onto the photocatalytic substrate; and a reflector positioned adjacent each UV light source for reflecting UV light toward the photocatalytic substrate. Each of the specific embodiments differ in either the particular housings for the foregoing components parts which adapt the invention for insertion into different positions within an HVAC return air system. For example, in one specific embodiment, the inventive photocatalytic air purification is configured within a housing which fits within return ductwork in a standard plenum-type ceiling grid commonly found in institutional and educational institutions. In another specific embodiment, the inventive photocatalytic air purification unit is configured within a housing that is placed in line with HVAC return ductwork, with the airflow passing first over the particulate filter and then onto the photocatalytic substrate. Still another specific embodiment of the present invention entails a housing which is adapted to be retrofit in-line with existing ductwork on roof-top HVAC units and/or installed in a new HVAC or retrofit HVAC system, such as those exceeding ten ton capacities, and consists of a generally rectilinear housing having a plurality of particulate filters within the housing on the upstream air flow side, a plurality of photocatalytic metal substrates immediately downstream the particulate filters and a plurality of UV lamps and associated reflectors downstream the photocatalytic metal substrates. The entire rectilinear housing is configured to slidably retrofit into existing return air ductwork in high capacity rooftop HVAC blower units.

In accordance with a second general embodiment of the present invention, there is provided a photocatalytic air purification system which is housed in a portable floor-standing housing and comprises generally; a particulate filter; a HEPA filter; a motor and fan for propelling airflow; a substrate powder coated with a photocatalyst; a UV light source for irradiating UV light on the substrate; and controls for operating the motor and fan either by a direct or a sensed switched input in response to manually applied inputs or in response to sensed conditions, such as a chemical sensor or particulate sensor.

The scope of the invention is indicated in the appended claims. It is intended that all changes or modifications within the meaning and range of equivalents are embraced by the claims.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

BRIEF DESCRIPTIONS OF THE DRAWINGS

The foregoing summary, as well as the following detailed description of preferred embodiments of the invention, will be understood when read in conjunction with the appended drawings. For the purpose of illustrating the invention, there is shown in the drawings embodiments which are presently preferred. It should be understood, however, that the invention is not limited to the precise arrangements and configurations shown.

DETAILED DESCRIPTION OF THE PREFERRED EMBODIMENTS

The present invention is directed to a system for and a method of making a PCO air filtration system using a substrate with titanium dioxide powder coated thereon. Because of the inventive powder coating process described herein, the inventive PCO air filtration system is more durable and has a longer lifetime than prior art PCO air filtration systems using substrates with titanium dioxide conventionally coated thereon using a liquid coating process.

The inventive method of powder coating titanium dioxide onto a substrate of a PCO unit presents advantages over conventional liquid coatings. For one, powder coating titanium dioxide onto a substrate of a PCO unit allows for better control over the coating thickness on the substrate and over the uniformity of the coating thickness.

In addition, the performance characteristics of a titanium dioxide coating layer formed from a powder coating process match or exceed the characteristics achieved from conventional solvent based coatings. Powder coating provides an extremely durable finish and has bonding capabilities superior to traditional wet coatings. In addition, it provides excellent chemical resistance.

In one preferred embodiment of the invention, Degussa P25 titanium dioxide particles are used. Degussa P25 titanium dioxide particles are composed of approximately 80% titanium dioxide in anatase form and of approximately 20% titanium dioxide in rutile form. The average particle size of Degussa P25 titanium dioxide agglomerate particles used in a preferred embodiment of this invention is approximately 20 µm. Titanium dioxide particles having other average particle sizes are considered to be within the scope of the invention.

In one aspect of the present invention, fine particles of titanium dioxide are grounded into even finer particles. The fine titanium dioxide particles are then mixed with plastic resin powders. This blend comprises a solvent-free mix of plastic resins and fillers that melt and fuse together when heated. The formulation variables are critical to the processing and performance characteristics.

Plastic resins that can be used for the inventive powder coating process include thermoplastic resins and thermosetting resins. A thermoplastic powder coating melts and flows when heat is applied, but continues to have the same chemical composition once it cools to a solid coating. Thermoplastic powders that can be used for powder coating include, but are not limited to, terephthalate ester-based resin such as polyethylene terephthalate (PET), polyvinyl chloride, polyolefins, nylon, polyester, and polyvinylidene fluoride. Terephthalate ester based resins having 2,2-dimethylpropanediol as the dominant diol and having a glass transition of the cured resin being about 74 degrees Centigrade have been found to be the most useful resins in the present invention.

Like thermoplastic resins, thermosetting powder coatings also melt when exposed to heat. However, after they flow to form a continuous film, thermoplastic resins chemically crosslink on additional heating. The final coating has a different chemical structure than the applied powder. The thermosetting powders that can be used for powder include, but are not limited to, epoxys, polyester hybrids, urethane polyesters, polyester TGICs (triglycidyl isocyanurate), acrylics, and combinations thereof.

In another aspect of the present invention, the substrate to be coated is thoroughly cleaned to remove grease and other contaminants. With raw aluminum substrates, oils and greases are removed in weak alkali or neutral detergent solutions and the surface is etched to remove heavy oxides. After rinsing, the aluminum may be dipped into a chromate or phosphate solution to form a conversion coating on the aluminum. This film is chemically attached to the aluminum. After rinsing the aluminum is finally rinsed in demineralized water. The conversion coating serves two functions: (1) it presents a surface to the powder which favors adhesion more than the oxides that form very readily on aluminum surfaces; and (2) it reduces the incidence of film corrosion. The use of demineralized water reduces the presence of chemical salts on the aluminum surface. These salts have been found to cause corrosion in humid conditions.

Any metal substrate that can hold an electrostatic charge and withstand the heat of the curing process can be powder coated. In the preferred embodiment of the invention, the metal substrate is formed of high quality raw aluminum. Tests have shown that titanium dioxide adheres stronger to aluminum than to other comparable materials with similar strength characteristics. In addition, aluminum has been shown to be a flexible material. Nonetheless, other materials, such as copper, steel, stainless steel, FeCrAlY alloy, ceramic, and other materials known in the prior art for use in forming a substrate in a PCO air filtration systems, are also within the scope of the invention.

In a preferred embodiment of the invention, a dry powder comprising titanium dioxide particles is admixed with a polymeric resin to form a titanium dioxide/resin mixture. After the powder preparation step, the titanium dioxide/resin mixture is then electrostatically charged (positively charged) in a spray gun and carried by low velocity air to the surface of the substrate (negatively charged) to be coated. The titanium dioxide-resin powder mix is sprayed onto intricate surfaces of the substrate, which maintains a uniform finish across the entire substrate. The electrostatic charge holds the powder particles in place while the substrate is cured in an oven. The heat of the oven causes a chemical reaction to occur causing the titanium dioxide powder to cure and become impregnated in the substrate. Resistant to chipping and fading, the titanium powder coated substrate formed from the above-described process will remain stable providing many years of constant photocatalyst activity.

The preferred embodiments of the inventive air filtration system generally includes a pleated particulate filter that is a MERV 8 through a HEPA rated filtration media, a UV light source, and a photocatalytic unit comprising either of an aluminum honeycomb panel as in the institutional unit embodiment or an aluminum mesh screen as in the portable unit embodiment. In each photocatalytic unit, the aluminum substrate (whether in honeycomb form or in mesh form) is powder coated with the titanium dioxide/resin mixture.

The titanium dioxide/resin mixture preferably consists of about 70% (wt. %) P25 hydrophilic fumed titanium dioxide (Degussa AEROXIDE® $TiO_2$ P25) having an approximate average particle size of 20 μm before mixing and about 30% (wt. %) of a terephthalate ester-based resin, such as polyethylene terephthalate (PET). The formulation of 70% P25 titanium dioxide and 30% terephthalate ester-based resin has unexpectedly been found to provide improved results in terms of improved efficiency of the PCO air filtration system. While the foregoing is the preferred titanium dioxide/resin mixture composition, other mixture compositions have also been found useful to form a photocatalyitic substrate useful in UV light activated photocatalytic air purification units. For example, it has been found that the titanium dioxide may be present between 60% and 85% by weight of the polymer resin, with the most preferred range being between about 62% by weight and 75% by weight of the resulting titanium dioxide/resin mixture.

The improved efficacy is caused by a more efficient PCO reaction mechanism, which maximizes airflow exposure to the titanium dioxide coating.

During admixing with the polymeric resin, the titanium dioxide particles tend to agglomerate and exhibit an average particle size of about 35.3 μm. Additionally, during the curing process, the titanium dioxide particles agglomerate to provide a resulting post-cured average particle size of about 134 μm.

The institutional unit embodiment contains an aluminum honeycomb panel substrate, while the portable unit embodiment contains a pleated woven aluminum mesh screen matrix. In both embodiments, UV light sources are situated between the particulate filter and the titanium dioxide coated substrate. One or more reflectors are positioned adjacent to the UV light sources to reflect UV light toward the photocatalytic unit. The UV light sources and the reflectors are positioned in a manner so as to equilibrate the intensity of UV light across the surface of the photocatalytic unit.

The inventive PCO air filtration system can exist in many forms. One preferred embodiment comprises an institutional unit having a PCO air filtration system comprising a honeycomb panel powder coated with titanium dioxide photocatalysts, a UV 36 Watt Philips lamp rated at 8,500+ hours life that emits UV light having a wavelength between 190-400 nm (preferably at 253.7 nm), and a particulate filter that is a MERV 8 or higher pleated filter. UV light at 253.7 nm has been found to be highly effective in exciting the titanium dioxide coating and thereby also effective in decomposing biological airborne contaminants. This particular institutional unit embodiment can have an airflow capacity of up to 2,000 CFM (Cubic Feet Per Minute). Because the institutional unit embodiment is designed for integration into an existing ventilation system with its own power, fans may not be necessary in the institutional unit embodiment.

Turning now to the accompanying Figures, in which like structural and/or functional features are designated by like reference numerals, FIGS. 1, 4A-4D and 5 illustrate an embodiment of the PCO air filtration system 100 of the present invention configured to be placed in-line in the return air ductwork of an HVAC system.

Figure 1:
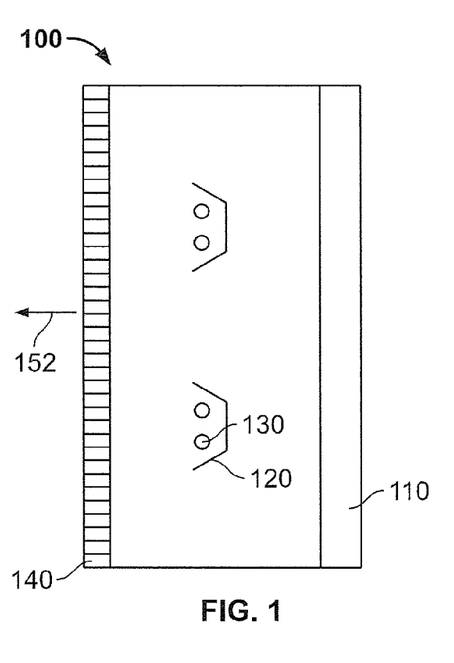
FIG. 1 provides an open side view of one preferred institutional unit embodiment of the invention.

FIG. 1 provides a side view of a first embodiment of a PCO air filtration system 100 of the present invention adapted for institutional installations within the return air ductwork of a HVAC system. FIGS. 4A-4D are diagrammatic illustrations of the device illustrated in FIG. 1. In each of the institutional unit embodiments of the invention, there is provided a structural housing 151 which serves to contain the functional elements of the air filtration system 100 and is capable of being fitted or retrofitted within the ductwork in an HVAC system.

Housing 151 serves as the support structure for a particulate filter 110 which is retained within a flange or seat formed (not shown) in the housing 151, for a photocatalytic substrate 140 which is retained within a flange or seat 154 formed in the housing 151, for a ballast 122 which controls at least one UV light source 130 removably connected to electrical connectors 124, and for at least one reflector element 120, adjacent each of the at least one UV light sources 130, configured to reflect UV light from the UV light source 130 onto the photocatalytic substrate 140.

Figure 2:
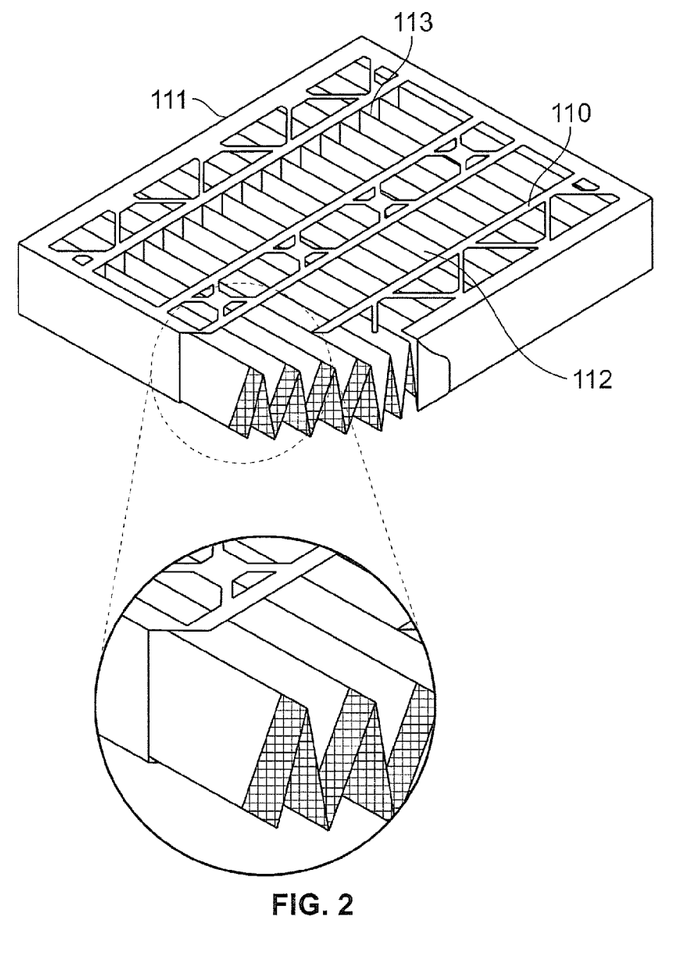
FIG. 2 provides a perspective view of the particulate filter illustrated in FIG. 1.

In operation, airflow 152 enters the PCO air filtration unit 100 and first passes through a particulate filter 110. An enlarged view of the particulate filter 110 is provided in FIG. 2. The particulate filter 110 is comprised of a frame 111, a pleated media 112, and moisture resistant media separators 113. The pleated media 112 may be formed of a synthetic material and may be laminated to a galvanized steel backing to stabilize the media during operation. The frame 111 and moisture resistant media separators 113 ensure integrity of the pleated media 112 during operation. MERV 8 or MERV 11 particulate filters are preferably employed as the particulate filter media 112. Examples of suitable filter media 112 are GLASSFLOSS Z-Line Air Cleaner Filters which are rigidly constructed utilizing high quality MERV 8 or MERV 11 rated filtration media, backed with a metal mesh to prevent sagging.

After passing the particulate filter 110, airflow 152 travels towards the photocatalytic substrate 140, passing around reflector elements 120 and UV light sources 130 and onto the photocatalytic substrate 140, whereupon the airflow 152 is photocatalytically treated. In the institutional embodiments, the substrate 140 may be formed of any suitable geometric structure known in the art, including, but not limited to, honeycomb, fins, mesh, fibrous structure, or a filamentous structure. Preferably, the substrate material is formed in a substantially rigid honeycomb configuration. The substrate 140 material is preferably aluminum. However, other materials, such as copper, steel, stainless steel, FeCrAlY alloy, ceramic, or any other metals or materials known to be conducive to receiving and to adherent coating of a photocatalyst, particularly titanium dioxide applied by electrostatic powder coating, may also be used.

Figure 3:
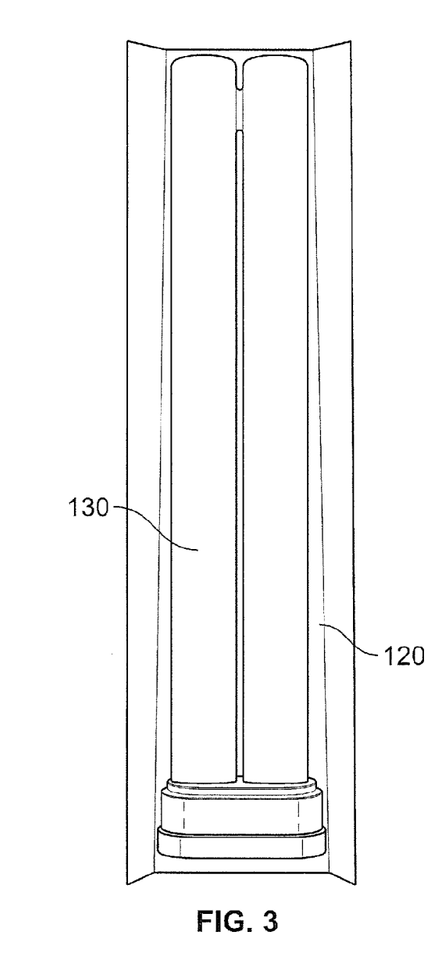
FIG. 3 provides a perspective view of the UV light source and the reflector illustrated in FIG. 1.
Figure 4A:
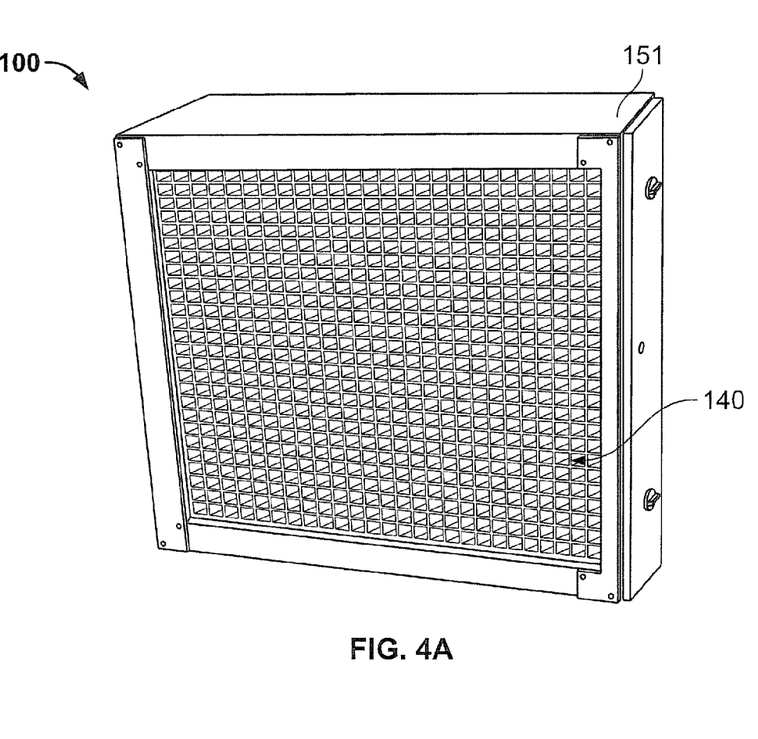
FIG. 4A provides a perspective view of the preferred institutional unit embodiment illustrated in FIG. 1.
Figure 4B:
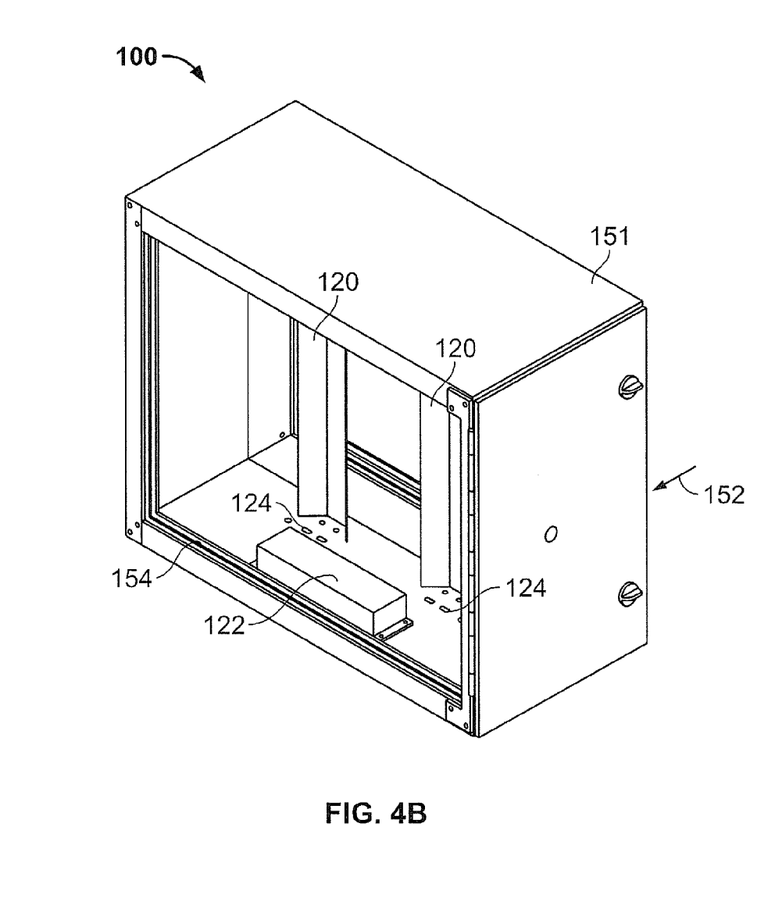
FIG. 4B is a perspective, fragmentary view of the embodiment illustrated in FIG. 4A.
Figure 4C:
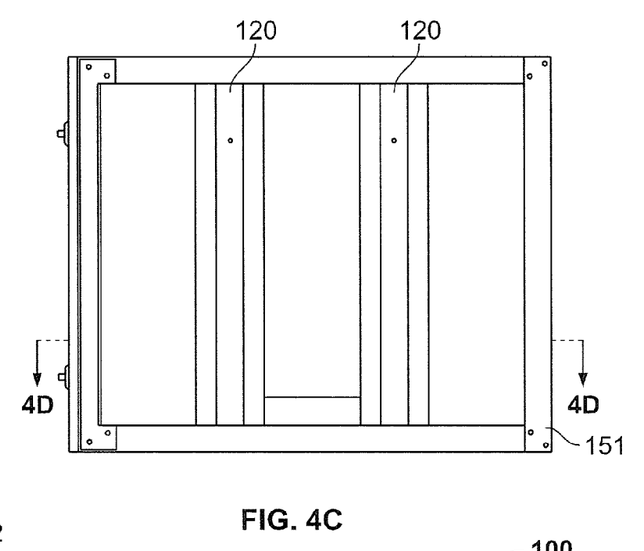
FIG. 4C is a side elevational, fragmentary view of the embodiment illustrated in FIG. 4B.
Figure 4D:
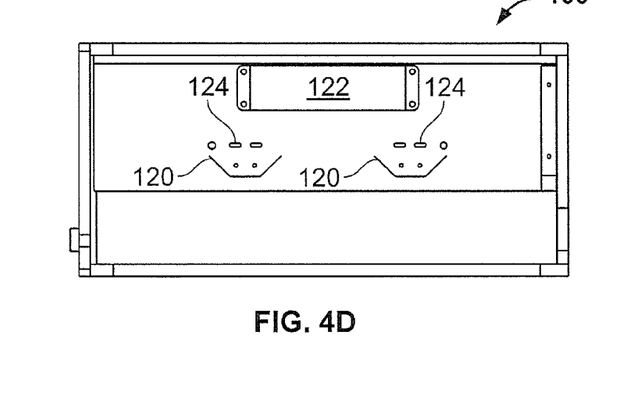
FIG. 4D is a cross-sectional view taken along line D-D of FIG. 4C.
Figure 5:
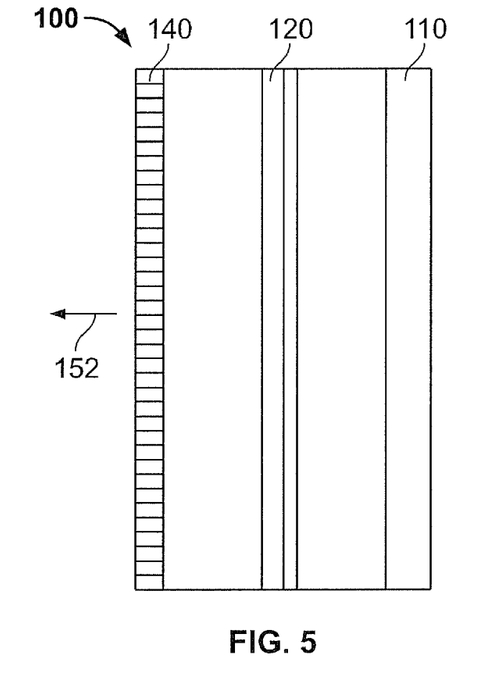
FIG. 5 is a top elevational view, fragmentary view of the embodiment illustrated in FIG. 1.

As airflow 152 leaves the particulate filter 110 and makes contact with the surface of the titanium dioxide coating on the substrate 140, the titanium dioxide layer coated on the substrate 140 reacts with organic contaminants in the air. This reaction takes place as UV light from UV light sources 130, with reflectors 120 positioned behind the UV light sources 130, irradiate the titanium dioxide coating layer on the substrate 140. The UV light sources 130 attach to the housing 151. A closer perspective view of one UV light source is provided in FIG. 3. The reaction occurring at the surface of the titanium dioxide coating causes VOCs and organic contaminants to disintegrate through reactions with oxygen ($O_2$) and/or hydroxyl radicals (OH).

Figure 9:
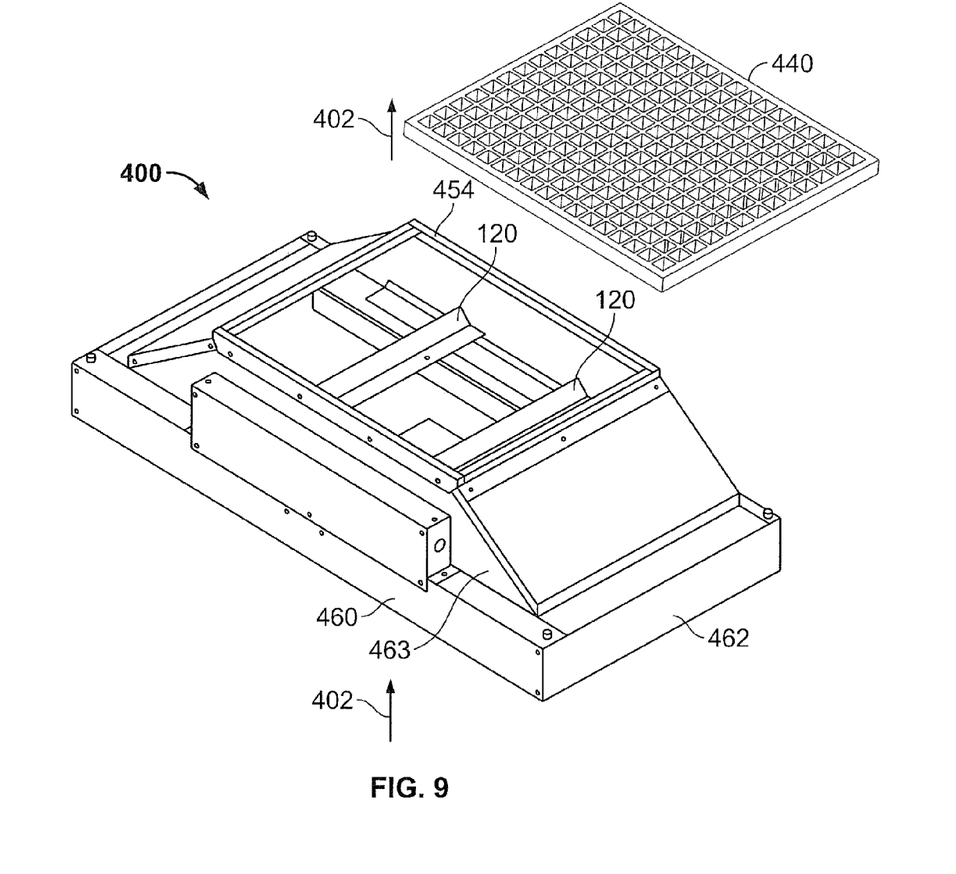
FIG. 9 is a perspective, fragmentary view of an alternate embodiment of the present invention adapted for installation into a ceiling panel grid.
Figure 10:
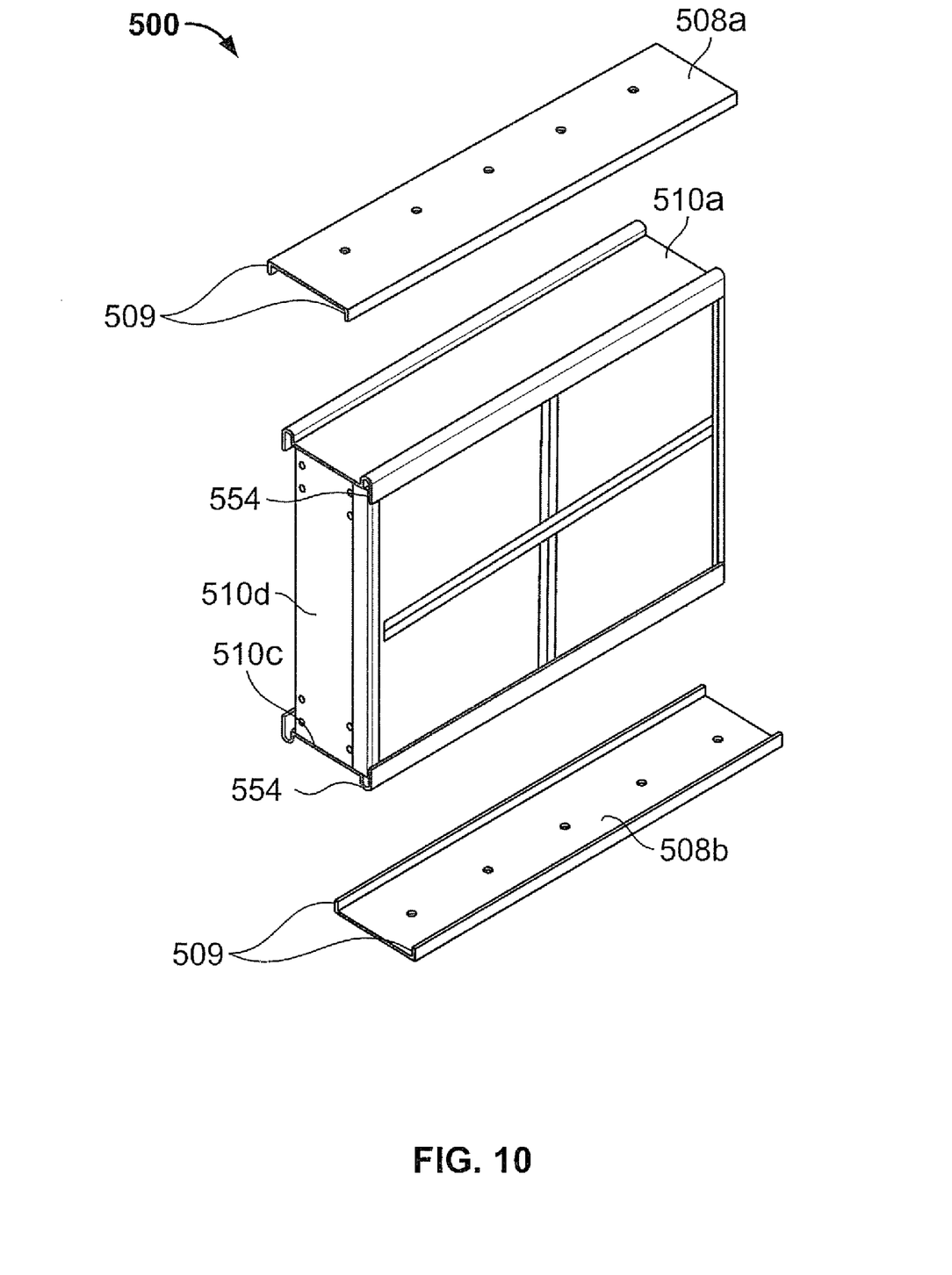
FIG. 10 is a perspective view of an alternate embodiment of the present invention adapted for, but not limited to, high-capacity HVAC systems, such as rooftop units and indoor or outdoor air handler systems.

FIGS. 1, 4A-4D and 5 illustrate an exemplary embodiment of an institutional unit. Alternative embodiments of institutional units are illustrated in FIGS. 9 and 10. FIG. 9 illustrates an embodiment of the institutional PCO air filtration unit 400 adapted for installation into a return HVAC line in a standard institutional ceiling grid. PCO air filtration unit 400 comprises generally of a housing 460 having a first rectilinear section 462 and a second generally trapezoidal shaped section 463 which concentrates airflow 402 into a smaller surface area as it passes across the reflector elements 120, a UV light source (not shown), and a PCO substrate 440 which is retained within flange or seat 454 of housing 460.

Figure 11:
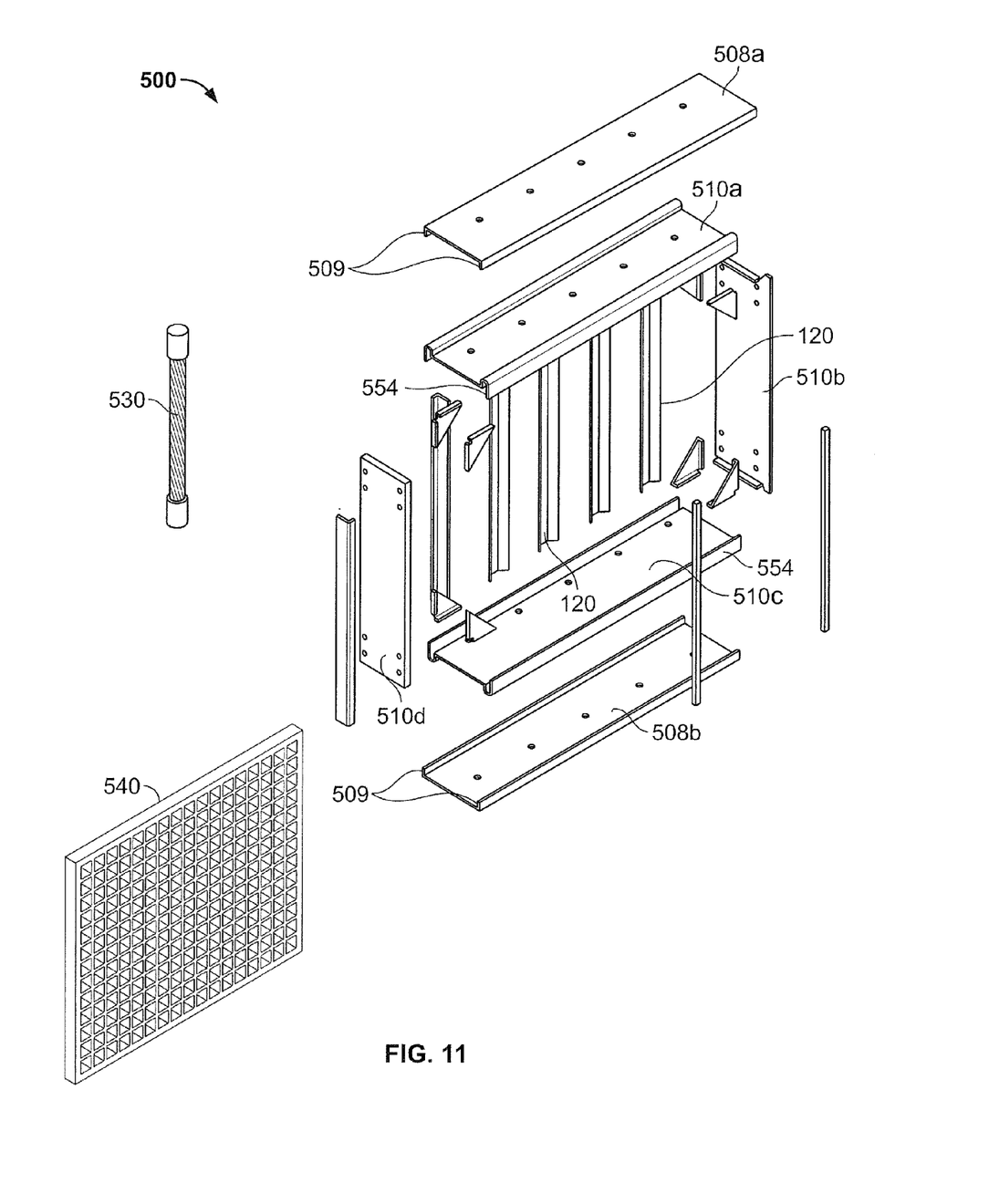
FIG. 11 is a perspective, exploded view of the embodiment illustrated in FIG. 10.

Still a further embodiment of the present invention is illustrated in FIG. 10 in which there is shown a PCO filtration system 500 for high-capacity HVAC units. A generally rectilinear housing adaptable to slide in and slide out of HVAC units on rail-like elements is formed by slide-in elements 510a-510d assembled to form a generally rectangular housing. Slide-in elements 510a and 510c have seating elements 554 for retaining a PCO substrate 540. Upper rail 508a and lower rail 508b each have seating flanges 509 that extend across the entire length of the rails. During installation, slide-in elements 510a and 510c slide onto upper rail 508a and lower rail 508b. The seating elements 554 of the slide-in elements 510a and 510c abut against the seating flanges 509 of the upper rail 508a and the lower rail 508b. An exploded view of the present invention depicted in FIG. 10 is illustrated in FIG. 11. Because of its intended application in high capacity HVAC systems, plural particulate filters, plural UV light sources 530, plural reflector elements 120, and plural PCO substrates 540 are preferably employed to increase the effective surface area of contact between the air flow and the PCO substrate. Those skilled in the art will understand and appreciate that multiple institutional units may be placed in parallel or in series to increase the resultant PCO air filtration capacity of the present invention. Although alternative configurations are possible and within the scope of the invention, the slide-in assembly will generally be configured downstream of particulate air filters.

Figure 6:
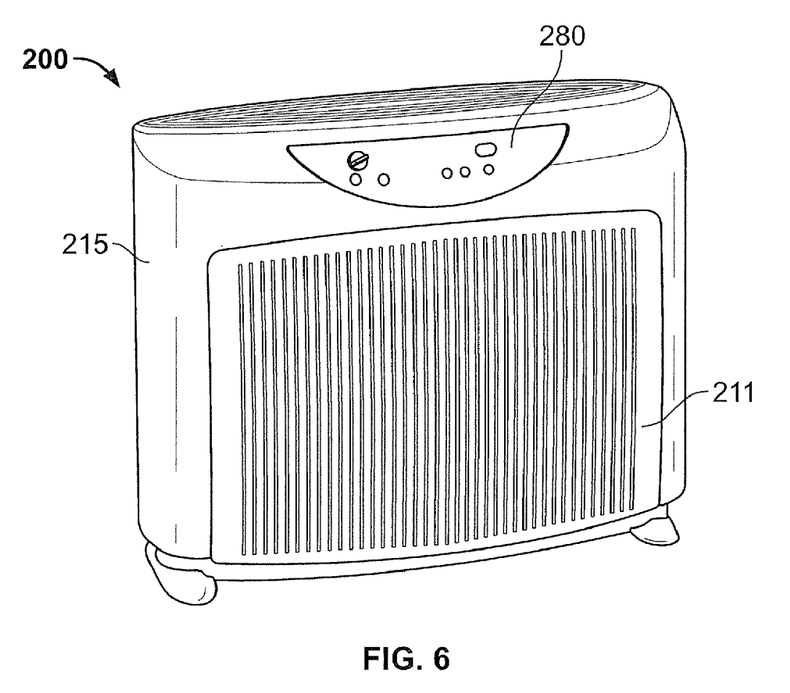
FIG. 6 provides a perspective view of one preferred portable unit embodiment of the invention.
Figure 7:
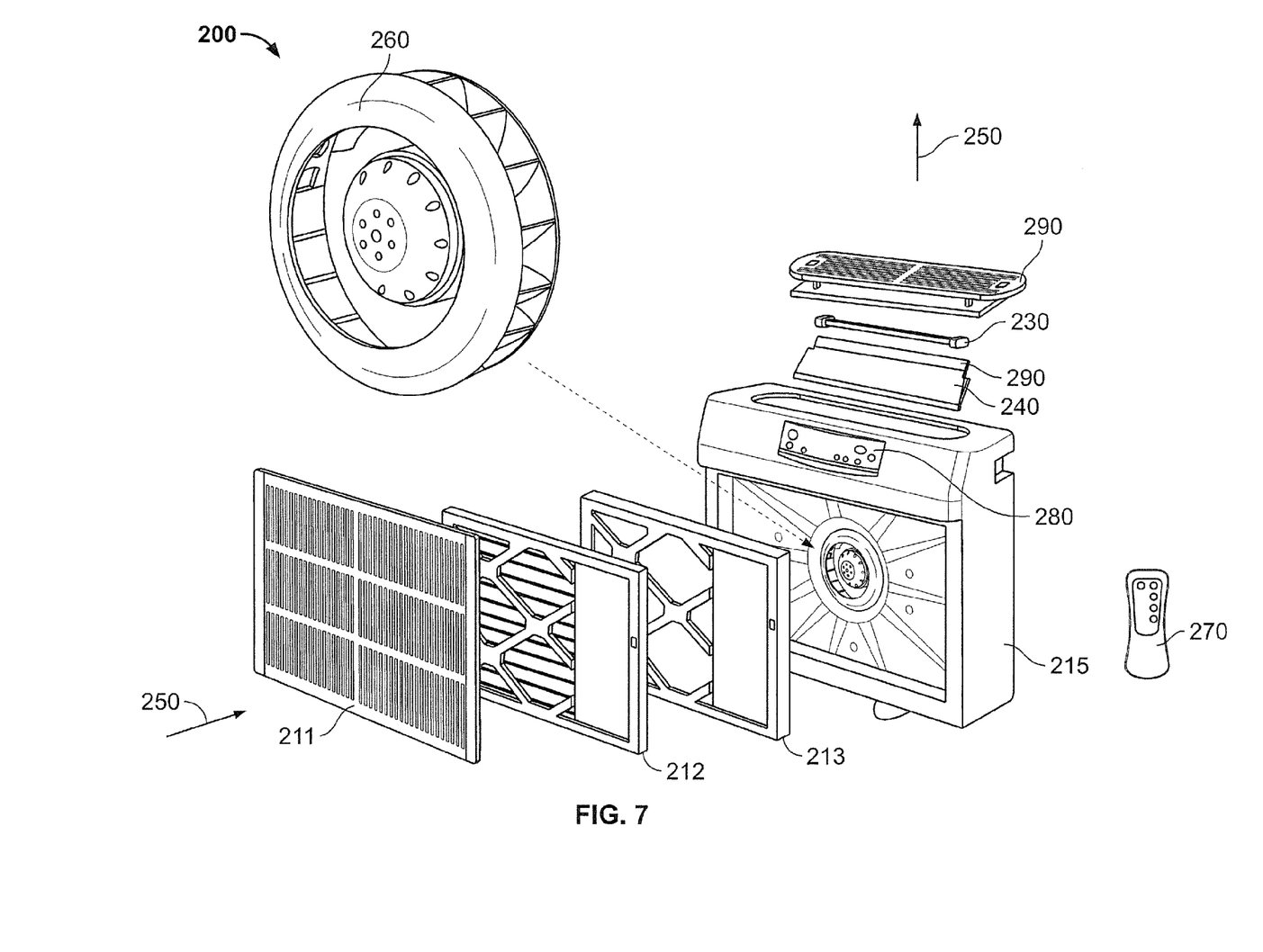
FIG. 7 provides an exploded view of the preferred portable unit embodiment illustrated in FIG. 6.

Another general embodiment of the PCO air filtration system comprises a portable unit which is preferably floor standing, but may be configured as a table-top unit. FIG. 6 provides a perspective front view of the portable unit embodiment of the PCO air filtration system 200. An exploded view of the portable unit embodiment is illustrated in FIG. 7.

Similar to the institutional unit embodiment, the portable unit embodiment also employs a UV light source 230 with a reflector 290. The portable embodiment unit may also include a pleated particulate filter 212 and may also include a HEPA filter 213. One difference between the portable unit embodiment and the institutional unit embodiment is that the PCO unit of the portable unit employs a substantially flexible pleated aluminum mesh screen matrix 240 powder coated with titanium dioxide, instead of the honeycomb panel substrate 140 in the institutional unit embodiment. The portable unit embodiment may also include various electronic controls located in a panel 280, such as, but not limited to, an infrared motion sensor, remote control, fan speed controls, or chemical sensors to actuate the device. The portable unit may also include a remote control 270 for controlling the PCO air filtration system 200.

The portable unit is encased in a housing 215, which can be of any suitable material, such as high impact ABS (Acrylonitrile-butadiene-styrene) plastic. Other types of material commonly used to provide housing for an apparatus are within the scope of the invention. During operation of the portable unit, airflow 250 is suctioned into the portable unit via a motor fan 260. Upon entry into the portable unit through an air inlet grill 211, airflow 250 enters into a particulate filter 212. The particulate filter 212 may be of any kind that is known in the art.

This particulate filter 212 is designed to capture all large particles, such as pollen, hair, and dust. The particulate filter 212 also ensures a longer life for a HEPA filter 213 that is positioned behind the particulate filter 212. The back side of the particulate filter 212 may comprise an active carbon for absorbing and dissolving odor or other toxic gases in airflow 250.

After passing through the particulate filter 212, airflow 250 next enters the HEPA filter 213. Various types of HEPA filters can be used. In one preferred embodiment, a hospital grade HEPA is used for removing allergens, such as mold, fungus, spores, tobacco smoke, insecticide dust, dust mites, and particles that are larger than 0.3 μm. The HEPA filter 213 may incorporate an extra active carbon layer, located in the middle of the HEPA filter 213, for eliminating odors or toxic gases. Furthermore, the HEPA filter 213 may have an additional filtration and sponge around the HEPA filter 213 for preventing air leakage. This addition improves the portable unit's airflow and filtration capacity in terms of CFM (Cubic Feet Per Minute).

After exiting the HEPA filter 213, airflow 250 is propelled by a motor fan 260 towards an aluminum mesh screen matrix 240 which disintegrates organic compounds in airflow 250. In one embodiment of the invention, the aluminum mesh screen matrix 240 is in a pleated and woven form. The aluminum mesh screen matrix 240 is powder coated with titanium dioxide. When a UV light source 230 irradiates UV light on the aluminum mesh screen matrix 240, oxidation of organic compounds in airflow 250 into water and harmless gases occurs on the titanium dioxide surface.

The one or more UV light sources 230 and the one or more reflectors 290 are positioned in a maimer so as to equilibrate the intensity of UV light across the surface of the aluminum mesh screen matrix 240. In one preferred embodiment, the one or more UV light sources are comprised of a 253.7 nm germicidal UV lamp. Other UV lamps known in the prior art can also be used and are also within the scope of the invention.

Figure 8:
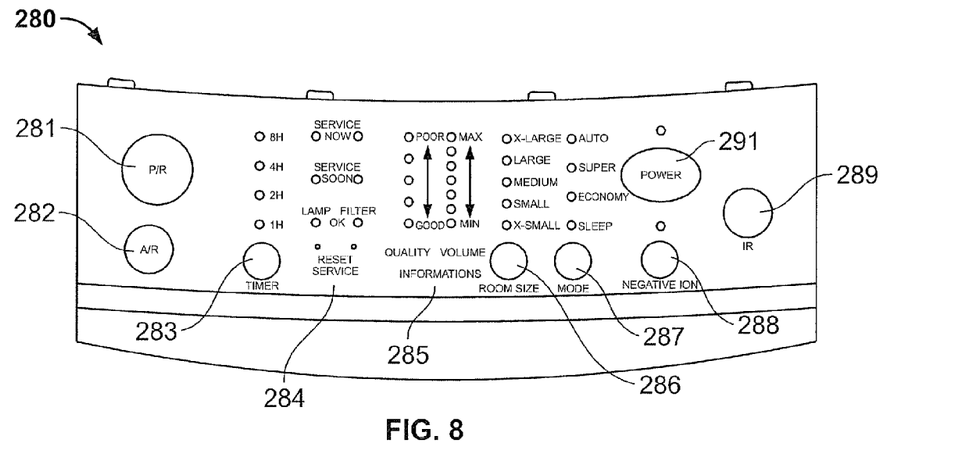
FIG. 8 illustrates a control panel of the embodiment illustrated in FIG. 6.

As illustrated in FIG. 6, the portable unit embodiment may incorporate a control panel 280, which is shown in greater detail in FIG. 8. The control panel 280 comprises an array of sensors, indicators, and a power button 291. The following is a list of possible sensors and detectors. An infrared motion sensor 281 detects the motion of a moving object in an 180 degree angle and automatically adjusts the motor fan's 260 speed upward or downward in response to detected motion or lack thereof. An air quality sensor 282 detects air quality and may also adjust the motor fan's 260 speed upward or downward in response to the detected air quality. The timer 283 allows the user to set the air filtration system to run at 1, 2, 4 or 8 hours. The service indicator 284 for filter and lamp lights up when filters or lamps need to be replaced. The air quality and volume indicators 285 indicate whether the air is of good quality or poor quality. The room size control 286 allows the user to select the relevant room size. The sizes can be x-large, large, medium, small or x-small. The control mode 287 allows the user to set the portable unit in four settings/speeds: sleep, economy, super, and auto. The negative ion generator 288 purifies and freshens the air. This is done as the negative ion generator 288 emits a stream of negative ions into the air, thereby resulting in cleaner and fresher air due to the electrostatic settling of dust and the invigorating effect of breathing negative ions. The infrared remote control receiver 289 allows for remote control and settings of available features.

The above-described methods for powder coating titanium dioxide onto a substrate and PCO air filtration systems are example implementations. The implementations illustrate possible approaches for powder coating titanium dioxide onto a substrate of a PCO air filtration system. The actual implementation may vary from the configurations discussed. Moreover, various other improvements and modifications to the PCO air filtration system may occur to those skilled in the art, and those improvements and modifications will fall within the scope of the invention as set forth in the claims below.

Long term testing of the institutional embodiments 100, 400 and 500 was conducted in the Lewisville, Tex. Independent School District over a period of six years to test for the effect of the inventive PCO air filtration units on absenteeism rates as an indicator of air quality. Institutional PCO air filtration units, as described above, were installed in nine public schools. When compared to the pre-installation absenteeism rates, the elementary schools exhibited a 0.53% attendance increase in the first year after implementation of the inventive PCO system, with subsequent increases of 0.15% in the second year and 0.39% in the third year. In the middle schools, the first year results showed an attendance increase of 0.71%, with subsequent attendance increases of 0.41% and 0.40% over the prior year. These results demonstrate a statistically significant increase in overall school attendance during the period of the study, and indicated an increase in overall attendance, and a decrease in absenteeism, in the schools retrofitted with the inventive PCO air purification system when compared with schools in which the inventive PCO air purification system was not present.

Analytical testing conducted on a first institutional embodiment of the present invention 100, in which airborne samples of a variety of VOCs were exposed to the PCO system of the present invention, yielded significant reductions in the VOC content of the treated sample after 24 hours, as reflected in Table I, below:

TABLE I

| Constituent | Starting Concentration (ppbv) | Concentration at 60 Minutes (ppbv) | Concentration at 24 Hours (ppbv) |
| --- | --- | --- | --- |
| Benzene | 11.2 | 4.83 | 0.45 |
| Bromomethane | 5.37 | 4.46 | ND (Not Detected) |
| Carbon Tetrachloride | 10.5 | 5.01 | ND |
| Chlorobenzene | 11.3 | 3.07 | ND |
| Chloroethane | 6.93 | 4.55 | ND |
| Chloroform | 9.90 | 4.88 | 0.22 |
| Chloromethand | 4.93 | 5.43 | ND |
| 1,2-Dibromoethane | 11.0 | 3.78 | ND |
| 1,2-Dichlorobenzene | 11.9 | 1.93 | ND |
| 1,3-Dichlorobenzene | 12.7 | 2.21 | ND |
| 1,4-Dichlorobenzene | 12.7 | 2.32 | ND |
| 1,1-Dichloroethane | 9.16 | 4.58 | ND |
| 1,1-Dichloroethene | 8.45 | 4.24 | ND |
| Dichlorodifluoromethane | 5.27 | 5.45 | 0.50 |
| Dichlorodifluroroethane | 4.08 | 4.70 | ND |
| 1,2-Dichloroethane | 10.6 | 4.85 | ND |
| Cis-1,2-Dichloroethene | 10.1 | 4.37 | ND |
| Dichloromethane | 8.7 | 4.88 | ND |
| 1,2-Dichloropropane | 9.97 | 4.45 | ND |
| Ethylbenzene | 12.2 | 2.02 | ND |
| Styrene | 12.6 | ND | ND |
| Toluene | 13.2 | 4.09 | 0.71 |
| Vinyl Chloride | 4.77 | 4.02 | ND |
| o-Xylene | 12.2 | 0.98 | ND |

The present invention may be embodied in other specific forms without departing from its spirit or essential characteristics. The described embodiments are to be considered in all respects only as illustrative and not restrictive. Therefore, the scope of the invention is not limited to the specific exemplary embodiment described above. All changes or modifications within the meaning and range of equivalents are intended to be embraced herein.

As used in this application, the articles "a" and "an" refer to one or more than one (i.e., to at least one) of the grammatical objects of the article. By way of example, "an element" means one element or more than one element.

What is claimed is:

1. A method for applying a photocatalyst onto a substrate useful in a photocatalytic oxidation air filtration system comprising the steps of:
   a. mixing a metal oxide photocatalyst with a polymeric resin to form a photocatalyst-resin mixture comprised of about 70% by weight of titanium dioxide and about 30% by weight of polymeric resin;
   b. electrically charging the photocatalyst-resin mixture;
   c. spraying the photocatalyst-resin mixture onto the substrate to form a photocatalyst powder-coated substrate; and
   d. heating the photocatalyst powder-coated substrate.

2. The method of claim 1, wherein the photocatalytic oxidation air filtration system further comprises:
   a. a particulate filter;
   b. a motor fan for propelling airflow;
   c. the photocatalyst powder-coated substrate; and
   d. a UV light source for irradiating UV light on the photocatalyst powder-coated substrate.

3. The method of claim 2, wherein the substrate is woven.

4. The method of claim 1, wherein the photocatalytic oxidation air filtration system further comprises:
   a. a particulate filter;
   b. the photocatalyst powder-coated substrate;
   c. at least one UV light source for irradiating UV light on the substrate; and
   d. at least one reflector positioned adjacent the at least one UV light source for reflecting UV light toward the substrate.

5. The method of claim 4, wherein the particulate filter is a MERV 8 or higher pleated filter.

6. The method of claim 1, wherein the substrate has a structure selected from the group consisting of: a honeycomb, fins, a mesh, a fibrous structure, or a filamentous structure.

7. The method of claim 1, wherein the titanium dioxide is P25 titanium dioxide having an average particle size of about 134 μm on the substrate.

8. The method of claim 1, further comprising the step of heating the substrate for a time and at a temperature sufficient to cure the photocatalyst-resin mixture on the substrate.

9. The method of claim 1, wherein the substrate comprises aluminum.

10. The method of claim 1, wherein the polymer resin further comprises a terephthalate ester-based resin.

* * * * *